US 9,788,874 B2

(12) United States Patent
Clasbrummel et al.

(10) Patent No.: US 9,788,874 B2
(45) Date of Patent: Oct. 17, 2017

(54) BONE PLATE SYSTEM FOR OSTEOSYNTHESIS

(71) Applicant: Merete Medical GmbH, Berlin (DE)

(72) Inventors: Bernhard Clasbrummel, Balingen (DE); Curt Kranz, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 446 days.

(21) Appl. No.: 14/385,723

(22) PCT Filed: Mar. 28, 2013

(86) PCT No.: PCT/DE2013/100117
§ 371 (c)(1),
(2) Date: Sep. 16, 2014

(87) PCT Pub. No.: WO2013/163985
PCT Pub. Date: Nov. 7, 2013

(65) Prior Publication Data
US 2015/0094773 A1    Apr. 2, 2015

(30) Foreign Application Priority Data
May 3, 2012    (DE) .................. 10 2012 103 894

(51) Int. Cl.
*A61B 17/80* (2006.01)
*A61B 17/86* (2006.01)

(52) U.S. Cl.
CPC ...... *A61B 17/8057* (2013.01); *A61B 17/8033* (2013.01); *A61B 17/8052* (2013.01); *A61B 17/8605* (2013.01)

(58) Field of Classification Search
CPC ............ A61B 17/8033; A61B 17/8052; A61B 17/8057
See application file for complete search history.

(56) References Cited

U.S. PATENT DOCUMENTS 2,662,988 A    12/1935    McKim
3,741,205 A    6/1973    Markolf et al.
(Continued)

FOREIGN PATENT DOCUMENTS

AT    406446    5/2000
DE    3113639    5/1982
(Continued)

OTHER PUBLICATIONS

International Search Report for PCT/DE2013/100117 dated Jul. 18, 2013.
(Continued)

*Primary Examiner* — Andrew Yang
(74) *Attorney, Agent, or Firm* — Andrus Intellectual Property Law, LLP

(57) ABSTRACT

A bone plate system is for osteosynthesis with a bone plate, a bone screw, the screw head of which has, at least in sections, a surface structure, a further bone screw, the screw head of which has, at least in sections, a surface structure, a through-hole, which is configured to hold the bone screw polyaxially, a further through-hole, which is associated with the through-hole and configured to hold the further bone screw, a perforation which connects the through-hole and the further throughhole, and a bulge, which is formed opposite to the perforation on the through-hole, extending the latter, hi the screwed-in state, the bone screw and the further bone screw are affixed at a fixed angle in many dimensions by virtue of the screw heads of the bone screw and the further bone screw being secured against a relative notion in relation to one another and in relation to the bone plate by a tensioned multi-point mount, in which attachments of the bone screw are formed in the through-hole at both transition regions between the bulge and the through-hole section respectively adjacent to the bulge.

9 Claims, 3 Drawing Sheets

(56) References Cited

U.S. PATENT DOCUMENTS

Figure 1:
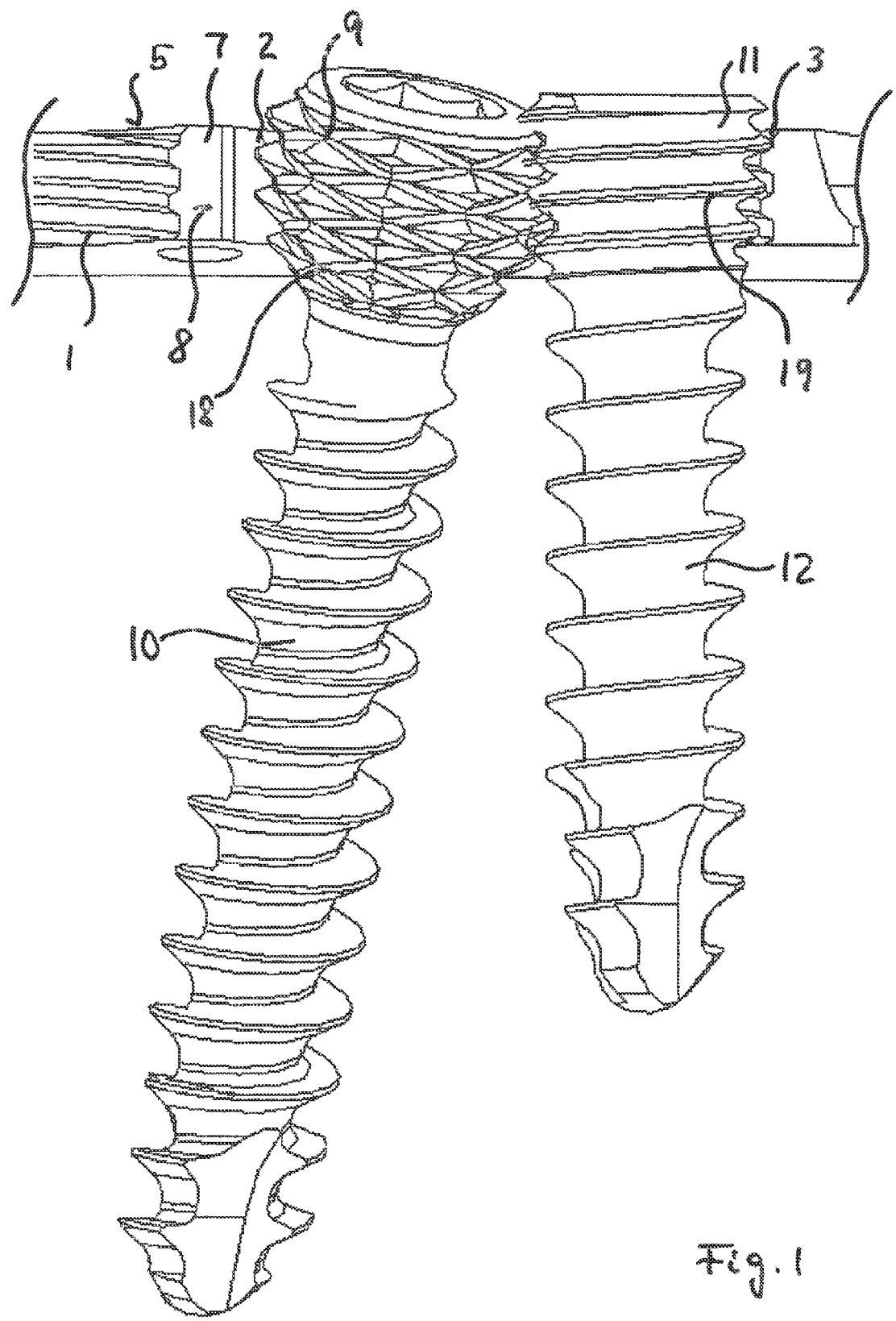

| | | |
|---|---|---|
| 3,757,591 A | 9/1973 | Taylor |
| 4,408,601 A | 10/1983 | Wenk |
| 4,454,876 A | 6/1984 | Mears |
| 4,616,634 A | 10/1986 | Vargas Garcia |
| 4,720,225 A | 1/1988 | Burt |
| 4,903,691 A | 2/1990 | Heinl |
| 4,959,065 A | 9/1990 | Arnett et al. |
| 5,529,075 A | 6/1996 | Clark |
| 5,709,686 A | 1/1998 | Talos et al. |
| 6,129,728 A | 10/2000 | Schumacher et al. |
| 6,203,545 B1 | 3/2001 | Stoffella |
| 6,206,883 B1 | 3/2001 | Tunc |
| 6,293,949 B1 | 9/2001 | Justis et al. |
| 6,306,140 B1 | 10/2001 | Siddiqui |
| 6,398,783 B1 | 6/2002 | Michelson |
| 6,423,068 B1 | 7/2002 | Reisberg et al. |
| 6,669,701 B2 | 12/2003 | Steiner et al. |
| 6,716,957 B2 | 4/2004 | Tunc |
| 6,719,759 B2 | 4/2004 | Wagner et al. |
| 6,730,091 B1 | 5/2004 | Pfefferle et al. |
| 6,886,799 B2 | 5/2005 | Yamanashi |
| 7,008,428 B2 | 3/2006 | Cachia et al. |
| 7,354,441 B2 | 4/2008 | Frigg |
| 7,468,069 B2 | 12/2008 | Baynham et al. |
| 7,655,029 B2 | 2/2010 | Niederberger et al. |
| 7,771,457 B2 | 8/2010 | Kay et al. |
| 7,976,570 B2 | 7/2011 | Wagner et al. |
| 8,118,848 B2 | 2/2012 | Ducharme et al. |
| 8,246,661 B2 | 8/2012 | Beutter et al. |
| 8,632,545 B2 | 1/2014 | Sarangapani et al. |
| 8,758,346 B2 * | 6/2014 | Koay ............... A61B 17/8014 606/282 |
| 2002/0045897 A1 | 4/2002 | Dixon et al. |
| 2002/0045901 A1 | 4/2002 | Wagner et al. |
| 2002/0183752 A1 | 12/2002 | Steiner et al. |
| 2003/0078668 A1 | 4/2003 | Michelson |
| 2004/0018228 A1 | 1/2004 | Fischell et al. |
| 2004/0034356 A1 | 2/2004 | LeHuec et al. |
| 2004/0073218 A1 | 4/2004 | Dahners |
| 2004/0102778 A1 | 5/2004 | Huebner et al. |
| 2004/0167522 A1 | 8/2004 | Niederberger et al. |
| 2004/0215192 A1 | 10/2004 | Justis et al. |
| 2004/0236332 A1 | 11/2004 | Frigg |
| 2005/0015092 A1 | 1/2005 | Rathbun et al. |
| 2005/0049594 A1 | 3/2005 | Wack et al. |
| 2005/0065521 A1 | 3/2005 | Steger et al. |
| 2005/0085818 A1 | 4/2005 | Huebner |
| 2005/0124994 A1 | 6/2005 | Berger et al. |
| 2005/0165400 A1 | 7/2005 | Fernandez |
| 2005/0165401 A1 | 7/2005 | Pack |
| 2005/0182408 A1 | 8/2005 | Pfefferle et al. |
| 2005/0192577 A1 | 9/2005 | Mosca et al. |
| 2005/0261688 A1 | 11/2005 | Grady, Jr. et al. |
| 2006/0015102 A1 | 1/2006 | Toullec et al. |
| 2006/0173458 A1 | 8/2006 | Forstein et al. |
| 2006/0235396 A1 | 10/2006 | Sanders et al. |
| 2006/0241607 A1 | 10/2006 | Myerson et al. |
| 2007/0016205 A1 | 1/2007 | Beutter et al. |
| 2007/0123885 A1 | 5/2007 | Kirschman |
| 2007/0233106 A1 | 10/2007 | Horan et al. |
| 2007/0276386 A1 | 11/2007 | Gerlach et al. |
| 2008/0051786 A1 | 2/2008 | Jensen |
| 2008/0132955 A1 | 6/2008 | Frigg |
| 2008/0300637 A1 | 12/2008 | Austin et al. |
| 2009/0024172 A1 | 1/2009 | Pizzicara |
| 2009/0210010 A1 | 8/2009 | Strnad et al. |
| 2010/0256687 A1 | 10/2010 | Neufeld et al. |
| 2011/0264149 A1 | 10/2011 | Pappalardo et al. |
| 2011/0295325 A1 | 12/2011 | Wagner et al. |
| 2012/0265254 A1 | 10/2012 | Horan et al. |
| 2013/0190829 A1 | 7/2013 | Batsch et al. |

FOREIGN PATENT DOCUMENTS

| | | |
|---|---|---|
| DE | 102005044841 | 3/2006 |
| DE | 102006000948 | 10/2006 |
| DE | 102005042766 | 1/2007 |
| DE | 102005043285 | 1/2007 |
| DE | 69835968 | 5/2007 |
| DE | 102007005417 | 6/2008 |
| DE | 102010025001 | 12/2011 |
| EP | 0243114 | 11/1990 |
| EP | 1255498 | 11/2002 |
| EP | 1158916 | 7/2004 |
| EP | 1158915 | 9/2004 |
| EP | 1468655 | 10/2004 |
| EP | 1255498 | 11/2005 |
| EP | 1677693 | 7/2006 |
| EP | 1702577 | 9/2006 |
| EP | 1897509 | 3/2008 |
| EP | 1468655 | 5/2008 |
| EP | 1702577 | 11/2008 |
| EP | 2016918 | 1/2009 |
| FR | 2667913 | 4/1992 |
| FR | 2739151 | 3/1997 |
| FR | 2886535 | 12/2006 |
| WO | 9709000 | 3/1997 |
| WO | 9829058 | 7/1998 |
| WO | 0053110 | 9/2000 |
| WO | 0154601 | 8/2001 |
| WO | 02096309 | 12/2002 |
| WO | 2005041769 | 5/2005 |
| WO | 2005041796 | 5/2005 |
| WO | 2005053111 | 6/2005 |
| WO | 2006014436 | 2/2006 |
| WO | 2007025520 | 3/2007 |
| WO | 2009058969 | 5/2009 |
| WO | 2010059497 | 5/2010 |
| WO | 2010115403 | 10/2010 |
| WO | 2011076205 | 6/2011 |
| WO | 2011163092 | 12/2011 |
| WO | 2012/000627 | 5/2012 |

OTHER PUBLICATIONS

Easley, Mark E., M.D., et al., Current Concepts Review: Hallux Valgus Part II: Operative Treatment, Foot & Ankle International, vol. 28/ No. 6, 748-758 (Jun. 2007).

Miller, Michael J., DMP et al., Inverted Z-scarf Osteotomy for Hallux Valgus Deformity Correction: Intermediate-term Results in 55 Patients, The Journal of Foot and Ankle Surgery, 50: 55-61 (2011).

Dereymaeker, Greta, MD, PhD, Scarf Osteotomy for Correction of Hallux Valgus-Surgical Technique and Results as Compared to Distal Cheveron Osteotomy, The Hallux, vol. 5/ No. 3, 513-523 (Sep. 2000).

Steck, Jerome K., DPM, Long Z-Osteotomy: A Review and New Modification to Correct Troughing, The Journal of Foot and Ankle Surgery, vol. 40/ No. 5, 305-310 (Sep./Oct. 2001).

Adam, Stephanie P., DO et al., Outcomes after Scarf Osteotomy for Treatment of Adult Hallux Valgus Deformity, Clinical Orthopaedics and Related Research, 469: 854-859 (2011).

Trnka, Hans-Jorg, MD et al., Six First Metatarsal Shaft Osteotomies—Mechanical and Immobilization Comparisons, Clinical Orthopaedics and Related Research, No. 381, 256-265 (Mar. 10, 2000).

Aminian, Arash, M.D. et al., Scarf Osteotomy for Hallux Valgus Deformity: An Intermediate Followup of Clinical and Radiographic Outcomes, Foot & Ankle International, vol. 27/ No. 11, 883-886 (Nov. 2006).

Weil, Lowell Scott, DPM, Scarf Osteotomy for Correction of Hallux Valgus—Historical Perspective, Surgical Technique, and Results, The Hallux, vol. 5/ No. 3, 559-580 (Sep. 2000).

Vienne, Patrick, M.D. et al, Comparative Mechanical Testing of Different Geometric Designs of Distal First Metatarsal Osteotomies, Foot & Ankle International, vol. 28/ No. 2, 232-236 (Feb. 2007).

(56) References Cited

OTHER PUBLICATIONS

Lipscombe, Stephen, MRCS et al, Scarf Osteotomy for the Correction of Hallux Valugs: Midterm Clinical Outcome, The Journal of Food and Ankle Surgery, vol. 47/ No. 4, 273-277 ( Jul./Aug. 2008).
Barouk, Louis Samuel, MD, Scarf Osteotomy for Hallux Valgus Correction—Local Anatomy, Surgical Technique, and Combination with Other Forefoot Procedures, The Hallux, vol. 5/ No. 3, 525-557 (Sep. 2000).
Crevoisier, Xavier et al., The Scarf Osteotomy for the Treatment of Hallux Valgus Deformity: A Review of 84 Cases, Foot & Ankle International, vol. 22/ No. 12, 970-976 (Dec. 2001).
Coetzee, J. Chris, M.D., Scarf Osteotomy for Hallux Valgus Repair: The Dark Side, Foot & Ankle International, vol. 24/ No. 1, 29-33 (Jan. 2003).
Interventional Procedures Programme—Interventional procedure overview of surgical correction of hallux valgus using minimal access techniques, National Institute for Health and Clinical Excellence, p. 1, 9.
Comparison of Preoperative to Postoperative Measurement at 6 Weeks, 1 and 2 Years Postoperative, Table 1.
O'Briain, David E. et al., Use of a Geometric Formula to Improve the Radiographic Correction Achieved by the Scarf Osteotomy, Foot & Ankle International, vol. 33/ No. 8, 647-654 (Aug. 2012).
International Search Report for PCT/DE2010/075167, mailed Apr. 15, 2011.
Acevedo, Jorge I, Sammarco, V. James, Boucher, Henry R., Parks, Bert G., Schon, Lew C., Myerson, Mark S; Mechanical Comparison of Cyclic Loading in Five Different First Metatarsal Shaft Osteotomies; Foot & Ankle International, Aug. 2002; vol. 23, No. 8, pp. 711-716.
Cisar, J., Holz, U, Jenninger, w., Uhlig. Chr.; Die Osteotomie nach Ludloff bei der Hallux-valgus-Operation; Aktuelle Traumatol. 13; 1983; pp. 247-249.
Hyer, Christopher F., Glover, Jason P., Berlet, Gregory C., Philbin, Terrence, M, Lee, Thomas H.; A Comparison of the Crescentic and Mau Osteotomies for Correction of Hallux Valgus; Journal of Foot and Ankle Surgery; Mar./Apr. 2008; vol. 47, No. 2,; pp. 103-111.
Ludloff, Prof. Dr. K.; Die Beseitigung des Hallux valgus durch die schrage planta-dorsale Osteotomie des Metatarus I.; Arch. Klin. Chir.; 110:364-387; 1918.
Mau, C., Lauber, H.J.; Die operative Behandlung des Hallux valgus (Nachuntersuchungen); 1926, 197:361-377.
Sammarco, V. James; Surgical Strategies: Mau Osteotomy for Correction of Moderate and Severe Hallux Valgus Deformity; Foot & Ankle International; Jul. 2007; 28(7); pp. 857-864.
Saxena, Amol, McCammon, Derek; The Ludloff Osteotomy: A Critical Analysis; Journal of Foot and Ankle Surgery; 1997; vol. 36, No. 2, pp. 100-105.
Trnka, H.-J., Hofstaetter, S.G., Hofstaetter, J.G., Gruber, F., Adams Jr., S.B., Easley, M.E.; Intermediate-Term Results of the Ludloff Osteotomy in One Hundred and Eleven Feet; The Journal of Bone and Joint Surgery; Mar., 2008; vol. 90-A(3); pp. 531-539.
International Search Report for PCT/2006/001508, mailed Feb. 8, 2007.
"Orthopaedic Product News"", Aug. 2005, Retrieved from the Internet: URL:http://www.orthoworld.com/us_opn-2005-08.pdf [retrieved on May 26, 2009], p. 30, Hallux Valgus Correction with a Low Profile Locking Plate."
International Search Report for PCT/DE2010/000365, mailed Sep. 8, 2010.
Iselin, Lukas D. et al., Operative Management of Common Forefoot Deformities a Representative Survey of Australian Orthopaedic Surgeons, Foot & Ankle Specialist, vol. X/ No. X, 1-7 (2012).
International Search Report for PCT/DE2012/100248, dated Dec. 20, 2012.
International Search Report for PCT/IB2014/001111, mailed Sep. 16, 2014.

\* cited by examiner

BONE PLATE SYSTEM FOR OSTEOSYNTHESIS

CROSS-REFERENCE TO RELATED APPLICATIONS

This application is the U.S. national stage application of International Application PCT/DE2013/100117, filed Mar. 28, 2013, which international application was published on Nov. 7, 2013, as International Publication WO2013/163985 in English language. The international application is incorporated herein by reference, in entirety. The international application claims priority to German Patent Application No. 10 2012 103 894.5, which is incorporated herein by reference.

The invention relates to technologies in the field of bone plate systems for osteosynthes

BACKGROUND

Bone plate systems provide fixed-angle fixation, by means of associated screws, of a bone plate for osteosynthesis in the bodies of humans or animals, Numerous bone plate systems are known that generally include a bone plate with an arrangement of several through-holes and associated screws, In addition to so-called bone screws, i.e., screws that are screwed into the bone during the fixation process, provision can be made of fastening screws that are themselves not screwed into the bone but into a thread formed in the bone plate. Such fastening screws are then used, for example, for fixing the bone screws (see for example Documents EP 1 702 577 A2, WO 2006/014438 A1 and also AT 406 446 B). In the system for cervical vertebrae in Document DE 698 35 968 T2, use is also made of a fastening screw for affixing several bone screws.

A bone plate provided with oblong holes is disclosed in Document WO 20051041769 A1.

Fixed-angle plate-screw connections to osteosynthesis plates have the advantage of better anchoring of the bone plate to the bone. This is particularly advantageous with fractures near joints, as in this manner it is possible, to grip and fix bone fragments near joints more effectively. The advantage of fixed-angle plate-screw connections is even more significant in the case of osteoporotic fractures near joints because non-fixed-angle bone screws are unable to affix an osteoporotic bone as effectively.

Fixed-angle plate-screw connections can be classified as monoaxial and polyaxial plate-screw connections.

Examples of monoaxial fixed-angle plate-screw connections are given in Documents DE 10 2005 044 841 B4 or DE 10 2005 043 285 E33. These systems are characterized in that they have screw heads with male threads that intermesh with corresponding female threads of plates. If a screw is screwed in during an operation, the positive fit between the male thread of the screw head and the female thread of the bone plate effects a fixed-angle plate-screw connection during the last turns of the screwing-in process.

Furthermore, bone plate systems have been proposed in which bone screws are variable with respect to their swivel or angular position relative to the bone plate during use. Such a bone plate system is described, for example, in document DE 10 2006 000 948 A1, A bone plate having at least one screw for fixed-angle fixation is disclosed in document WO 2007/025520 A1, Another example of a polyaxial fixed-angle plate-screw connection is disclosed in DE 10 2005 042 766 B4. The embodiment described therein of a female thread from six female thread columns makes it possible to screw in spherical head screws having a special male thread in the polyaxial direction and to affix them in a fixed-angle manner during the last turns of the screwing-in process. Such plate-screw systems have become increasingly common in clinical practice due to clinical advantages of a polyaxial fixed-angle fixation option.

Document WO 2010/115403 A1 discloses a device for the fixed-angle fixation and compression of a fracture site on a bone. The disclosed bone plate is equipped with several individual holes, in each of which a bone screw can be screwed in. In combination with the individual holes, provision can be made for equipping the latter with a crescent-shaped hole extension, Document WO 2009/058969 A1 also relates to a bone plate system in which the bone plate is equipped with several individual holes for holding exactly one screw in each case. In the through-holes provision is made of columns with projections that, in the screwed-in state of the respective screw, intermesh with a thread on the screw head. The plurality of columns with projections are separated from one another in the respective hole by areas that are free from such projections and hence have a smooth surface.

Additionally, a bone plate system for osteosynthesis is disclosed in Document WO 2011/076205 A1 in which for affixing the bone plate to the bone a swivel screw is screwed into a swivel hole and a clamping screw is screwed into a clamping hole in such a way that, in the screwed-in state, the swivel screw and the damping screw are affixed at a fixed angle in many dimensions, the screw heads of the swivel screw and of the damping screw being secured against a relative motion in relation to one another and in relation to the bone plate, wherein the swivel screw and the clamping screw are each configured as a bone screw.

Additionally, Document DE 10 2007 005 417 A1 discloses a plate implant for use on the spinal column, in which each bone screw is screwed into an associated through-hole. The screw head of the bone screw is equipped with a thread that, in the screwed-in state, cooperates with intersecting lines or intersecting surfaces in each associated through-hole.

SUMMARY

The object of the invention is to propose improved technologies for bone plate systems for osteosynthesis that ensure optimum fixed-angle fixation in many dimensions of the screws inserted in the bone plate.

This object is achieved by a bone plate system for osteosynthesis as in independent claim 1. Embodiments are the subject matter of dependent subordinate claims.

Provision is made of a bone plate system for osteosynthesis having a bone plate, a bone screw, the screw head of which has, at least in sections, a surface structure, and a further bone screw, the screw head of which has, at least in sections, a surface structure. The bone plate has a through-hole suitable for holding the bone screw polyaxially, and also a further through-hole, which is associated with the through-hole and is suitable for holding the further bone screw. The through-hole and the further through-hole are connected to one another via a perforation, which extends over the entire thickness of the bone plate or a partial height so that corresponding through-holes are formed.

Provision is made of a bulge, which extends the through-hole and is arranged opposite to the perforation. In the screwed-in state, the bone screw and the further bone screw are affixed at a fixed angle in many dimensions, the screw heads of the bone screw and of the further bone screw being secured against a relative motion in relation to one another and in relation to the bone plate by means of a tensioned multi-point mount. The tensioned multi-point mount is formed with attachments of the bone screw in the through-hole at transition regions between the bulge and the respective through-hole section adjacent to the bulge. Preference is given to the transition regions being formed as corner regions in which the bone screw is attached in the screwed-in state. The bone screw is thus rigidly connected in the through-hole to both oppositely arranged transition regions.

The bulge of the through-hole forms an extension of the hole. Preferably, the through-hole is configured as a round hole. As an alternative or in addition, the further through-hole is also configured as a round hole.

By virtue of the screw head of the bone screw being supported on both transition regions in the, through-hole, the screw head is supported in two regions for which a connection line runs perpendicular to the connection axis between the through-hole and the further through-hole.

The screw head of the bone screw can extend into the bulge, at least in the screwed-in state. Preference is given, however, to the screw head not attaching in the bulge, but being spaced from the surface of the bulge outside the transition regions.

In an embodiment the tensioned multi-point mount can be configured in such a way that the attachments of the bone screw at both transition regions between the bulge and the respective through-hole section adjacent to the bulge give rise to a three-point fixation, which in addition to both transition regions involves the attachment of the screw head of the bone screw to the screw head of the further bone screw. The three-point fixation is uniquely suited for reinforcing the fixed-angle fixation in many dimensions. A further three-point fixation can be formed between the attachments in both transition regions and an attachment of the further bone screw in the further through-hole opposite to the perforation.

A preferred improvement makes provision such that radial projections and/or radial channels are formed, at least in sections, in the through-hole outside the bulge, with which the surface structure on the screw head intermeshes, at least in sections, in the screwed-in state of the bone screw. With the aid of the radial projections and/or radial channels, one or more thread turns with pitch can be formed. The thread can preferably be configured as a female v-thread. The radial projections and/or radial channels can be arranged in one or more columns, which are formed in the through-hole and extend from the upper side to the underside of the bone plate. in an alternative embodiment, the radial projections and/or radial channels are formed continuously from the edge of the bulge to the edge of the perforation between the through-hole and the further through-hole, preferably also in both halves of the through-hole. In the screwed-in state of the bone screw, the surface structure on the screw head can interlock with the radial projections and/or radial channels.

In an embodiment provision can be made such that radial projections and/or radial channels are formed, at least in sections, in the further through-hole, with which the surface structure on the screw head intermeshes, at least in sections, in the screwed-in state of the further bone screw. The statements made above with regard to the radial projections and/or radial channels of the through-hole likewise apply to the preferred embodiments.

An advantageous embodiment makes provision such that the bulge is configured with a crescent shape. In an embodiment, the outer contour of the bulge can correspond to a circular arc section, Wherein the associated radius of the circular arc section is smaller than the radius of the through-hole. Preference is given to the radius of the circular arc section of the bulge being at most about ⅔ of the radius of the through-hole. Further preference is given to the radius of the circular arc section of the bulge corresponding at most to about ½ of the radius of the through-hole.

Provision can be made such that the bulge has a smooth surface. The bulge is free of radial projections and radial channels. Nor is provision made of any thread in the bulge in this case.

In an advantageous embodiment, provision can be made such that a rectilinear distance between opposite ends of the bulge is smaller than the diameter of the through-hole. In a preferred embodiment, the rectilinear distance is at most ⅔ of the diameter of the through-hole. Further preference is given to the rectilinear distance between the opposite ends of the bulge being at most about half of the diameter of the through-hole.

An improvement can provide that the through-hole is formed with a spherical head holder opening towards the upper side of the bone plate and the screw head of the bone screw is formed as an associated spherical head, which in the screwed-in state of the bone screw is arranged, at least partially, in the spherical head holder of the through-hole, in the screwed-in state, the screw head of the bone screw, when held in the spherical head holder, can be interlockingly arranged therein. As an alternative or in addition, the further through-hole can be foxed with a spherical head holder opening towards the upper side of the bone plate in which the screw head of the bone screw, which is formed as an associated spherical head, intermeshes in the screwed-in state. In this respect provision can be made in an embodiment such that both the bone screw and the further bone screw are formed with a spherical head, which in the screwed-in state is arranged in a spherical head holder in each case.

A preferred improvement makes provision such that the spherical head is equipped with a first thread and a second thread, which are formed superimposed on the screw head. The first thread and the second thread can be, for example, a right-hand thread and a left-hand thread. In addition provision can be made of a further thread and/or horizontal circumferential grooves in the spherical head.

In a preferred embodiment, a swivel screw is formed with the bone screw, and a clamping screw is produced with the further bone screw. In the screwed-in state the swivel screw is introduced in an associated swivel hole, which is also the through-hole and which then allows different swivel positions of the bone screw. The clamping screw is held in a clamping hole formed by the further through-hole. Provision can also be made such that the through-hole as well as the further through-hole are configured as swivel holes, in particular if both bone screws are formed with a spherical head.

Without limiting the embodiments described in the following to the clamping and swivel screw combination, further alternative embodiments shall now be described in more detail This applies similarly to the use of the terms clamping hole and swivel hole as examples in the following. These terms relate to a through-hole and also to a further through-hole in general.

In a preferential manner, a development makes provision such that the bone plate is formed with an expansion region bordering the clamping hole in such a way that, as the clamping screw is screwed into the female thread of the clamping hole, the bone plate is at least partially yielding to the screwing pressure and deformable free of plastic deformation owing to the interaction between the male thread and the female thread, in this manner, as the screw head with a male thread is being screwed into the female thread, regions of the clamping hole can be deformed, not plastically, in particular elastically in such a way that the clamping hole matches the shape of the screw head and the screw is kept from unscrewing due to the circumferential tension. The embodiment making provision of the expansion region is preferably configured in such a way that the male thread is formed as a conical male thread and the female thread is formed as a cylindrical female thread.

The clamping screw can optionally be screwed in with the screw head completely in the through-hole. In this case the screw head is secured against turning by the elastic tension in each position on the one hand, but without the bone plate being irreversibly deformed, i.e., overstretched, in its plastic region on the other. In this manner it is possible for the clamping screw to be screwed in with great precision as far as necessary for affixing the bone plate securely on the bone and for effecting the clamping with the swivel screw, wherein it is simultaneously possible to ensure that the screw head, even in its most prominent regions, does not project past the bone plate so that the affixed bone plate as a whole together with the clamping screw—forms a unit that essentially adheres smoothly to the bone without elevations. In an embodiment provision can be made such that the bordering expansion region is configured, at least partially, as a bar or part of a ring.

In an embodiment provision can be made such that in the damping screw, the shank has a length equal to or shorter than the length of the shank of the swivel screw. in an embodiment the length of the shank of the clamping screw is at most half, preferably at most a third, of the length of the shank of the swivel screw. The shortened length of the damping screw compared to the length of the swivel screw contributes in particular to the multidimensionality of the swivel or angular positions of the swivel screw in relation to the bone plate. In an embodiment, the shank of the swivel screw can thus also be swiveled in a region below the bottom end of the shank of the clamping screw.

An advantageous embodiment makes provision such that in the clamping screw, a bone thread with a widening section is formed on the screw shank adjacent to the screw head and an essentially adjoining transition region is formed at the thread base of the conic male thread.

In a preferential manner, a development makes provision such that at least one further through-hole configured similarly to the swivel hole or to the damping hole and corresponding to the swivel hole and to the clamping hole is formed in the bone plate, that in the further through-hole a further bone screw is introduced, which is configured similarly to the swivel screw or to the damping screw, and that the screw head of the further bone screw is rigidly connected to the screw heads (e.g., with the spherical head and the screw head with the conical male thread) and to the bone plate in the screwed-in state. An arrangement of at least three through-holes associated with one another and in which a respective bone screw is screwed is formed in this embodiment. Provision can be made of any combination of swivel screws and clamping screws, wherein thread sections of the screw heads of the bone screws involved optionally interlock in pairs, thus bracing one another and being jointly secured against a relative motion on the bone plate.

Preferred embodiments will be explained in more detail in the following:

The swivel hole and the associated damping hole can be part of or form a so-called plate hole group with further through-holes. The bone plate can have a plurality of plate hole groups. Additional through-holes can be formed as round or oblong holes for the exact fit of screws with round, countersunk, spherical, pan, bulbous, or conical heads. A particularly advantageous swivel screw for the bone plate has a spherical screw head that is flattened on the head end (North Pole).

A preferred clamping screw is configured as a countersunk head screw with a cylinder thread below the countersunk head. To improve the contact surface, the shape of the under surface of the countersunk head screw can be rounded and configured to match the spherical shape of the swivel screw head. The length of the cylinder thread of the thread bolt is many times, for example, 0.9 times, greater than the plate thickness. Hence the cylinder thread of the damping screw is initially able to engage securely in the cylindrical counter thread of the plate and in the further course of the screwing process, press the swivel screw on the intended place in order to provide the greatest possible clamping effect. This is especially advantageous with slightly tilted swivel screws. During the process of rigid connection, the cylinder thread of the clamping screw projects slightly beyond the lower surface of the bone plate, which is why the beginning of the cylinder thread on the screw tip site can be configured as a self-tapping thread, thus enabling the cylinder thread to penetrate slightly into the bone to be screwed. The other and as a rule longer screw tip side portion of the thread bolt of the clamping screw is typically configured as a bone screw with a self-tapping thread.

The male thread of the clamping screw, which, is intended to engage in the counter thread of the bone plate, can be configured as a conical thread, wherein the angle of inclination of the cone to the longitudinal axis of the screw is smaller than the angle of inclination of the countersunk head.

During the use, the swivel screw can be initially screwed in polyaxially, enabling it to affix bone fragments and pull them to the plate. The clamping screw can then be screwed in and simultaneously affix itself and the swivel screw at a fixed angle during the final turns. The clamping screw itself acts as a monoaxial fixed-angle screw.

In an embodiment, the polyaxiality of the swivel screw is limited by the outer edge of the thread bolt of the swivel screw, which in the swiveled state abuts on the lower edge (corresponding to the side of the bone plate facing away from the screw head) of the swivel hole of the plate. In order to achieve a highly variable adjustment of the longitudinal axis of the swivel screw, preference is given to the bolt not having a thread in the region below the screw head. The lower side of the swivel hole advantageously has a supplementary bevel for widening a swivel radius of the swivel screw. Thus the longitudinal axis of the screw can be introduced in a variable manner, up to the maximum possible azimuth angle, in relation to the axis of the hole.

In order to prevent damage to the conical thread of the clamping screw from rubbing on the spherical head of the swivel screw, the thread can advantageously have rounded points.

In another exemplary embodiment, the surface of the swivel screw is configured in such a way that the round head surface of the swivel screw has longitudinal segments (e.g., twelve length segments) perpendicular to the equator of the screw head. Each longitudinal segment is configured with a female v-thread column in order to provide an interlocking abutment for the clamping screw. Hence an interlocking fixed-angle fixation of both screws can be effected in the following manner. The clamping screw has a conical male v-thread, which allows an interlocking, rigid connection to the plate by means of a conical female v-thread of the clamping hole on the one hand. The swivel screw is interlockingly fixed by means of its female thread columns on the screw head. The female thread columns on the swivel screw are configured in such a way that, for instance, the surface of the screw head part of the swivel screw still has enough spherical surface area so that neither thread damage no burr formation occur as the swivel Screw is being tightened.

In another advantageous embodiment, the side of the swivel hole can be equipped with at least one female v-thread column in order to confer greater angular stability to the assembly. Since the swivel screw can likewise be configured with preferably twelve female thread columns, said female v-thread columns on the side of the swivel hole can advantageously be configured with a matching or adaptable thread form.

Increased angular stability is achieved with the aid of such female thread columns formed on sides of swivel holes. This can be advantageous in bone plate systems for treating, for instance, femoral fractures. An obvious disadvantage of female thread columns in the side of the swivel hole is a limited possibility of drawing bone fragments together with the swivel screw, which is a consequence of the interlocking of the swivel screw with said female thread columns. in an embodiment, this disadvantage, i.e., a limited possibility of drawing fragments together, can nevertheless be used as an advantage from a clinical standpoint, as a certain degree of angular stability can be achieved just by the introduction of a swivel screw. After the introduction of a clamping screw, greater and sturdier angular stability of the swivel screw can then be achieved with the aid of said clamping screw.

By altering the site of the swivel hole, whether it is provided with at least one female v-thread column or not, it is also possible to predefine the degree of angular stability of the swivel screw, which allows an advantageous adaptation to clinical requirements.

DESCRIPTION OF PREFERRED EXEMPLARY EMBODIMENTS

Figure 2:
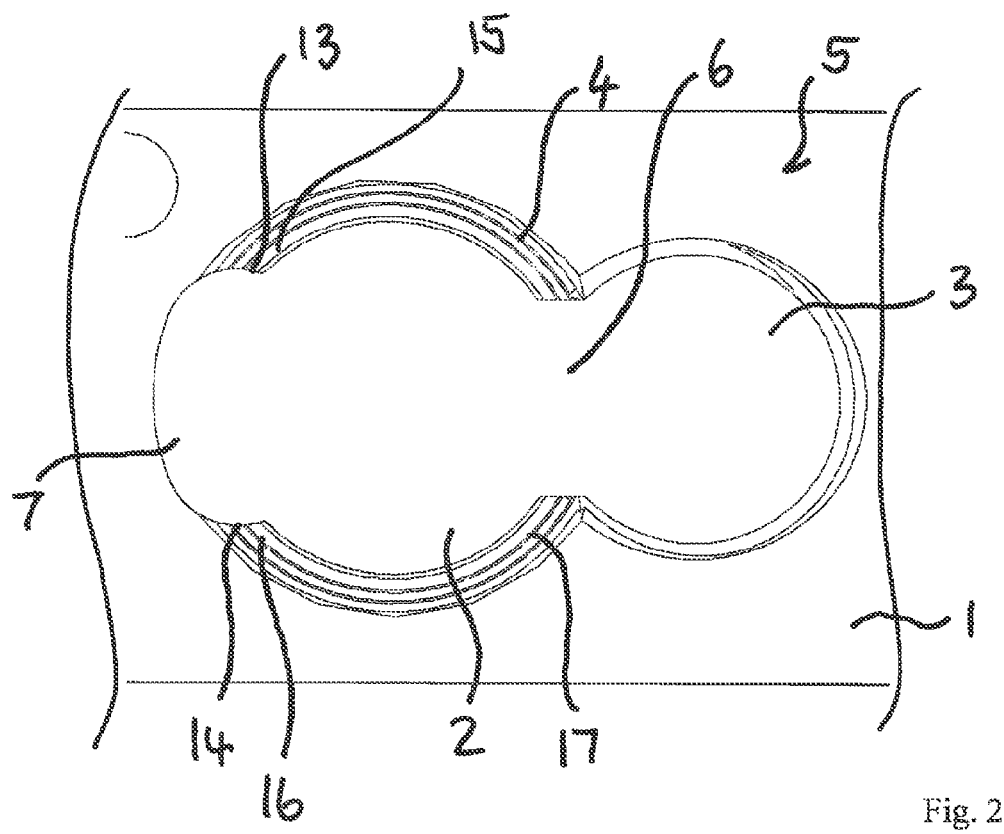
Figure 3:
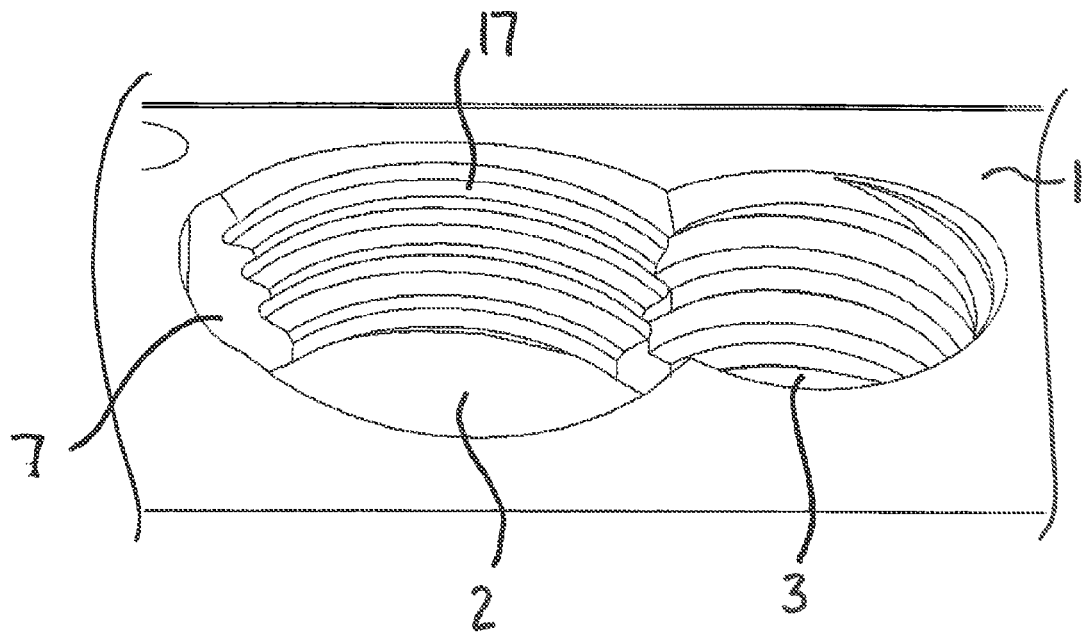
Figure 4:
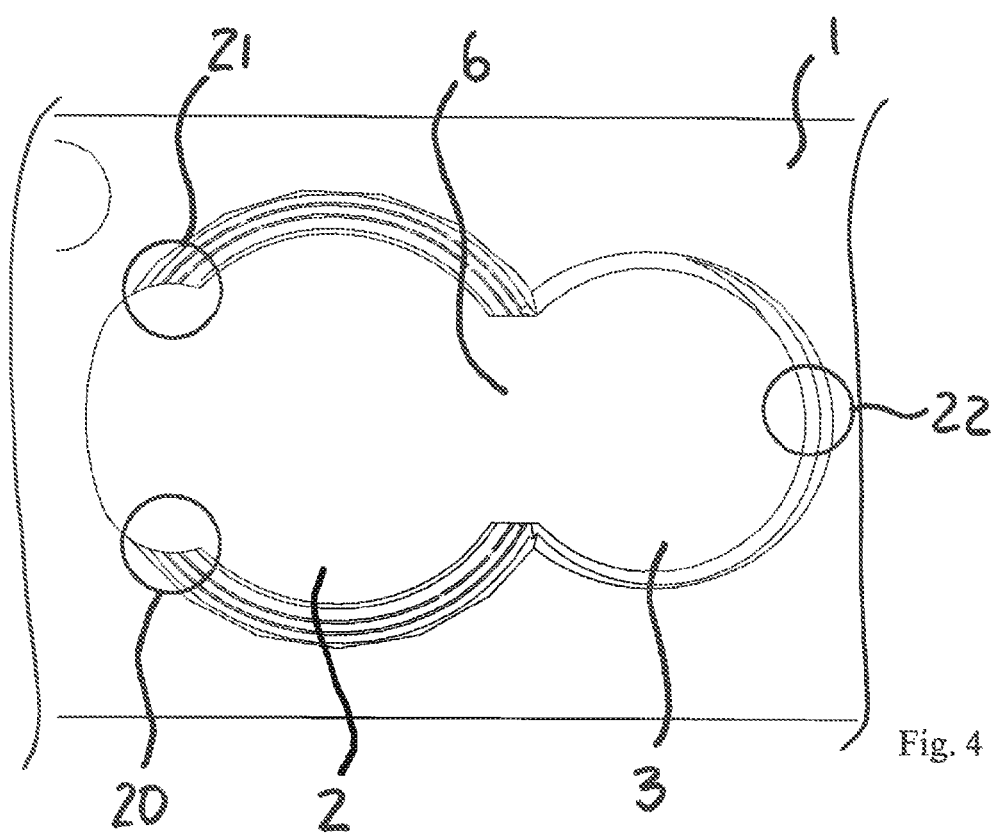

Additional exemplary embodiments shall be described in more detail in the following, with reference to figures of a drawing. Shown are:

FIG. 1 a schematic representation of a part of a bone plate system with a section of a bone plate and bone screws screwed into the same, FIG. 2 a schematic representation of a section of a bone plate viewed from above, FIG. 3 a schematic representation of the section of the bone plate from FIG. 2 viewed obliquely from above, and FIG. 4 a schematic representation of a tensioned three-point mount for the section of the bone plate from FIG. 2.

FIG. 1 is a schematic representation of a part of a bone plate system with a section of a bone plate 1 in which a through-hole 2 and a corresponding further through-hole 3 are formed, which in the exemplary embodiment shown form a swivel hole and an associated screw or clamping hole The through-hole 2 is produced with a spherical head holder 4, which opens towards the upper side 5 of the bone plate 1. Alternatively, provision can be made (not shown) such that both through-holes 2, 3 are formed with a spherical head holder.

According to FIG. 2 and FIG. 3, the through-hole 2 and the further through-hole 3 are connected to each other via a perforation 6 so that corresponding through-holes are formed As can be discerned most easily in FIG. 2, opposite the perforation 6 the through-hole 2 has a bulge 7, which has a smooth inner surface 8 in the exemplary embodiment illustrated.

In the screwed-in state (see FIG. 1), a screw head 9 of a bone screw 10 and a screw head 11 of a further bone screw 12 are rigidly connected to one another and thereby secured against a relative motion in relation to one another and in relation to the bone plate 1. The screw head 9 of the bone screw 10 is attached in corner regions 13, 14, in which the bulge 7 comes in abutment against adjacent through-hole sections 15, 16, which in turn are provided with continuous radial grooves 17 extending to the perforation 6.

The screw head 9 of the bone screw 10 is provided with a male thread 18, which is configured as a combination of a right-hand and a left-hand thread. The male thread 18 extends circumferentially around the spherical head of the bone screw 9. n the screwed-in state the male thread 18 intermeshes with the radial grooves 17 and with a thread profile 19 on the screw head 11 of the further bone screw 12.

FIG. 4 shows a schematic representation of a tensioned three-point mount. Circles 20, 21, and 22 symbolize the attachment of the screw head 9 of the bone screw 10 in the corner regions 14, 15 in the through-hole 2 on the one hand and an attachment of the screw head 11 of the further bone screw 12 in the further through-hole 3 opposite the perforation 6 on the other. Another three-point fixation arises between the attachments in the corner regions on the one hand and the contact between the screw heads 9, 11 of the bone screw 10 and the further bone screw 12 (not shown in FIG. 4).

The features disclosed in the present description, in the claims, and in the drawing can be of significance individually as well as in any combination for the realization of the various aspects.

The invention claimed is:

1. A bone plate system, for osteosynthesis, comprising:
   a bone screw, the screw head of which has, at least in sections, a surface structure,
   a further bone screw, the screw head of which has, at least in sections, a surface structure, and
   a bone plate, said bone plate having
   a through-hole, which is configured to hold the bone screw polyaxially,
   a further through-hole, which is associated with the through-hole and configured to hold the further bone screw,
   a perforation, which connects the through-hole and the further through-hole, and
   a bulge, which is formed opposite to the perforation on the through-hole, extending the latter,
   wherein in the screwed-in state, the hone screw and the further bone screw are affixed at a fixed angle in many dimensions in that the screw heads of the bone screw and of the further bone screw are secured against a relative motion in relation to one another and in relation to the bone plate by means of a tensioned multi-point mount in which attachments of the bone screw are formed in the through-hole at transition regions between the bulge and the respective through-hole section adjacent to the bulge.

2. The bone plate system as in claim 1, wherein radial projections and/or radial channels are formed, at least in sections, in the through-hole outside of the bulge, with which the surface structure on the screw head intermeshes, at least in sections, in the screwed-in state of the bone screw.

3. The bone plate system as in claim 1, wherein radial projections and/or radial channels are formed, at least in sections, in the further through-hole, with which the surface structure on the screw head intermeshes, at least in sections, in the screwed-in state of the further bone screw.

4. The bone plate system as in claim 1, wherein the bulge is configured with a crescent shape.

5. The bone plate system as in claim 1, wherein the bulge has a smooth surface.

6. The bone plate system as in claim 1, wherein a rectilinear distance between opposite ends of the bulge is smaller than the diameter of the through-hole.

7. The bone plate system as in claim 1, wherein the bulge is essentially formed mirror symmetrically to the extension of the line connecting the center points of the through-hole and of the further through-hole.

8. The bone plate system as in claim 1, wherein the through-hole is formed with a spherical head holder opening towards the upper side of the bone plate and the screw head of the bone screw is formed as an associated spherical head, which is at least partially arranged in the spherical head holder of the through-hole in the screwed-in state of the bone screw.

9. The bone plate system as in claim 8, wherein the spherical head is equipped with a first thread and a second thread, which are formed superimposed on the spherical head.

* * * * *